US010858596B2

(12) United States Patent
Adam et al.

(10) Patent No.: US 10,858,596 B2
(45) Date of Patent: Dec. 8, 2020

(54) SEPARATION OF FRACTIONS IN HYDROCARBON SAMPLES USING AN ACCELERATED SOLVENT EXTRACTOR (71) Applicant: Saudi Arabian Oil Company, Dhahran (SA)

(72) Inventors: Frederick M. Adam, Dhahran (SA); Zahra N. Almisbaa, Dhahran (SA); Mansour S. Alzayer, Dhahran (SA); Faisal Alrasheed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/294,308

(22) Filed: Mar. 6, 2019

(65) Prior Publication Data
US 2020/0283686 A1 Sep. 10, 2020

(51) Int. Cl.
*C10G 21/02* (2006.01)
*G01N 33/28* (2006.01)
(Continued)

(52) U.S. Cl.
CPC .......... *C10G 21/02* (2013.01); *B01D 11/0492* (2013.01); *C10G 21/14* (2013.01);
(Continued)

(58) Field of Classification Search
CPC ........ C10G 21/02; C10G 21/14; C10G 21/16; C10G 21/28; C10G 21/30; G01N 33/2823; G01N 33/2835
See application file for complete search history.

(56) References Cited

U.S. PATENT DOCUMENTS 4,865,741 A * 9/1989 Nolte .................. B01D 15/422
210/635
5,785,856 A 7/1998 Gleave et al.
(Continued)

FOREIGN PATENT DOCUMENTS

KR  101421077 B1  7/2014
KR  101507042 B1  4/2015

OTHER PUBLICATIONS

Bissada et al. "Group-type characterization of crude oil and bitumen. Part I: Enhanced separation and quantification of saturates, aromatics, resins and asphaltenes (SARA)." Organic geochemistry 95 (2016): 21-28.
(Continued)

*Primary Examiner* — Renee Robinson
(74) *Attorney, Agent, or Firm* — Leason Ellis LLP (57) ABSTRACT A method and a system for separating and recovering an entire liquid hydrocarbon sample using an accelerated solvent extractor is disclosed. In the method, a filter is inserted into a bottom portion of an extraction cell of the accelerated solvent extractor. An adsorbent is activated via heating in a furnace and then cooled. At least a portion of the adsorbent is then inserted into the extraction cell and a liquid hydrocarbon sample is introduced into the extraction cell on top of the adsorbent. The extraction cell comprising the sample is placed in a cell tray of the accelerated solvent extractor and the saturate, aromatics, and resins fractions of the sample are sequentially extracted using first, second and third solvents, respectively. The entire liquid hydrocarbon sample is extracted as a result of the method.

26 Claims, 7 Drawing Sheets (51) Int. Cl.
  *G01N 1/18*    (2006.01)
  *B01D 11/04*   (2006.01)
  *G01N 30/02*   (2006.01)
  *C10G 21/14*   (2006.01)
  *C10G 21/28*   (2006.01)
  *C10G 21/30*   (2006.01)
  *C10G 21/16*   (2006.01)

(52) U.S. Cl.
  CPC ............ *C10G 21/16* (2013.01); *C10G 21/28* (2013.01); *C10G 21/30* (2013.01); *G01N 1/18* (2013.01); *G01N 30/02* (2013.01); *G01N 33/2835* (2013.01); *G01N 2030/025* (2013.01); *G01N 2030/027* (2013.01)

(56) References Cited

U.S. PATENT DOCUMENTS

| | | |
|---|---|---|
| 9,255,475 B2 | 2/2016 | Zuo et al. |
| 2013/0067991 A1* | 3/2013 | Schabron ............... C10G 25/00 73/23.37 |
| 2013/0242288 A1* | 9/2013 | Kharrat ............. G01N 33/2835 356/51 |
| 2015/0036136 A1* | 2/2015 | Kharrat ................. G01N 33/28 356/326 |
| 2016/0169858 A1 | 6/2016 | Rogel et al. |
| 2018/0164273 A1 | 6/2018 | Sieben et al. |

OTHER PUBLICATIONS

Kettle. "Use of accelerated solvent extraction with in-cell cleanup to eliminate sample cleanup during sample preparation." Thermo Fisher Scientific (2013). 7 pages.

No Author. ASE® 200 Accelerated Solvent Extractor Operator's Manual. Document No. 031149, Revision 04, Dec. 1999. Dionex Corporation. 184 pages.

No Author. ASE® Solvent Controller Installation Instructions. Document No. 031277, Revision 03, Apr. 2000. Dionex Corporation. 18 pages.

Richter et al. "Accelerated solvent extraction: a technique for sample preparation." Analytical Chemistry 68.6 (1996):1033-1039.

Weiss et al. NIGOGA—The Norwegian Industry Guide to Organic Geochemical Analyses [online]. Edition 4.0 Published by Norsk Hydro, Statoil, Geolab Nor, SINTEF Petroleum Research and the Norwegian Petroleum Directorate. 2000. Retrieved Mar. 6, 2019. Available from World Wide Web: <http://www.npd.no/engelsk/nigoga/default.htm>. 102 pages.

International Search Report and Written Opinion in Corresponding PCT Application No. PCT/US2020/021380 dated Jun. 17, 2020. 13 pages.

* cited by examiner

| PARAMETER | STAGE 1 | STAGE 2 |
|---|---|---|
| Flush % | 35 | 40 |
| Static min | 70 | 50 |
| Pressure psi | 500 | 1000 |
| Temperature °C | 80 | 50 |
| Solvent | Hexane | toluene |
| Preheat min | 1 | 1 |
| Purge s | 20 | |
| Cycle | 1 | |

SEPARATION OF FRACTIONS IN HYDROCARBON SAMPLES USING AN ACCELERATED SOLVENT EXTRACTOR

TECHNICAL FIELD

The present disclosure is related to systems and methods for separating hydrocarbon samples. In particular, the present disclosure is related to systems and methods for separating fractions in hydrocarbon samples using an accelerated solvent extractor.

BACKGROUND

Fractionation processes and qualitative analyses for hydrocarbon-based compositions are vital for determining whether those compositions are useful for downstream operations, such as for use in the fuel industry. For example, gravimetric column chromatography can be used to perform fractionation and quantification methods on a hydrocarbon feed (e.g., crude oil) in which the feed is separated into saturate, aromatic, resin, and asphaltene fractions (SARA fractionation). SARA fractionation methods using gravimetric column chromatography are generally based on polarity differences between the separated fractions.

While gravimetric column chromatography is an effective way for performing a SARA fractionation, it generally requires a day-long experiment, which consumes high amounts of solvents and adsorbent material as well as being time intensive. As such, these experiments can be very costly due to their time-consuming and resource-consuming nature. Further, due to their duration, these methods can cause experimenters to be exposed to toxic chemicals for long periods of time. Accordingly, there is a need for fractionation and quantification methods that are more resource- and cost-efficient, and that can be accomplished faster than conventional methods.

SUMMARY

In accordance with one or more embodiments, method and systems of separating and recovering an entire liquid hydrocarbon sample using an accelerated solvent extractor are provided.

In a first aspect for the present method, a filter is inserted into a bottom portion of an extraction cell of the accelerated solvent extractor. An adsorbent is then inserted into the extraction cell such that the adsorbent occupies a substantial portion of the volume of the extraction cell. The liquid hydrocarbon sample is then introduced on top of the adsorbent in the extraction cell. The extraction cell comprising the hydrocarbon sample is placed into a cell tray of the accelerated solvent extractor. A saturate fraction of the hydrocarbon sample is extracted using a first solvent, and the saturate fraction is collected in a first collection vial. An aromatics fraction of the hydrocarbon sample is extracted using a second solvent, and the aromatics fraction is collected in a second collection vial. A resins fraction of the hydrocarbon sample is extracted using a third solvent, and the resins fraction is collected in a third collection vial. In the method, the entire liquid hydrocarbon sample is extracted.

In another aspect, the adsorbent is activated via heating within the accelerated solvent extractor and then cooled prior to insertion into the extraction cell. In a further aspect, the cooled, activated adsorbent is wetted with a solvent prior to insertion into the extraction cell. In a further aspect, the adsorbent material comprises silica. In a further aspect, the solvent for wetting the cooled, activated silica adsorbent is hexane. In another aspect, the silica adsorbent is heated at a temperature of approximately 400° C. in an oven for approximately 4 hours during activation. In a further aspect, the oven is subsequently cooled to 150° C. to cool the silica adsorbent.

In another aspect, the first, second, and third collection vials are placed under nitrogen gas to remove the first, second, and third solvents from the collected saturate, aromatic, and resins fractions, respectively. In a further aspect, the saturate, aromatic, and resin fractions are extracted sequentially from the liquid hydrocarbon sample.

In another aspect, the extracted fractions are qualitatively analyzed to determine the compositions of the respective fractions. The extracted fractions are analyzed via an analytical technique selected from the group consisting of mass spectrometry, NMR spectroscopy, gas chromatography, liquid chromatography, and supercritical chromatography.

In another aspect, the first solvent comprises hexane and the second solvent comprises toluene.

In another aspect, the extraction of the saturate fraction is performed at a different temperature and pressure than the extraction of the aromatic fraction and the resins fraction.

In another aspect, the liquid hydrocarbon sample is a diesel fuel sample. In yet another aspect, the liquid hydrocarbon sample is a crude oil sample.

In another aspect, the saturate fraction is extracted by introducing the first solvent into the extraction cell such that the first solvent interacts with the liquid hydrocarbon sample and causes the saturate fraction to pass through the filter and into the first collection vial. Similarly, the aromatic fraction is extracted by introducing the second solvent into the extraction cell such that the second solvent interacts with the liquid hydrocarbon sample and causes the aromatic fraction to pass through the filter and into the second collection vial. The resins fraction is extracted by introducing the third solvent into the extraction cell such that the third solvent interacts with the liquid hydrocarbon sample and causes the resins fraction to pass through the filter and into the third collection vial. In a further aspect, the extractions of the respective fractions are performed at different respective temperatures and pressures.

In another aspect, the maximum overlap of aromatics in the collected saturate fraction is 15%. In another aspect, the first solvent is selected from the group consisting of: hexane, cyclohexane, heptane, and isooctane. In another aspect, the second solvent is toluene or 95:5 blend of toluene and cyclohexane. In another aspect, the third solvent is selected from the group consisting of: acetone, chloroform, methanol, and a 1:4 blend of toluene and methanol.

In another aspect, the extraction cell is flushed with nitrogen gas between the extractions of each of the saturate fraction, the aromatics fraction, and the resins fraction. The nitrogen gas flushes the extraction cell of the solvent present from the previous extraction step. In another aspect, the adsorbent occupies 97 to 99% of the volume of the extraction cell and the hydrocarbon sample occupies less than 3% of the volume of the extraction cell.

According to at least one embodiment, a method of separating and recovering a liquid hydrocarbon sample using an accelerated solvent extractor is provided. In the method, an extraction cell that includes a tubular body packed with a filter at a bottom end and an adsorbent material disposed on top of the filter is prepared, such that the adsorbent material occupies at least 90% by volume of the tubular body. The hydrocarbon sample is introduced on top of the adsorbent material in the extraction cell. The extraction cell comprising the hydrocarbon sample is placed into a cell tray of the accelerated solvent extractor. At least one extraction is then performed using at least one solvent resulting in one or more fractions being individually extracted and collected. In a further aspect, the adsorbent material occupies at least 95% by volume of the tubular body. In another aspect, the adsorbent material occupies at least 98% by volume of the tubular body. In another aspect, the step of introducing the hydrocarbon sample results in the hydrocarbon sample being contained within a top 10% by volume of the adsorbent material.

DETAILED DESCRIPTION OF CERTAIN EMBODIMENTS OF THE INVENTION

The present application describes systems and methods for separating and recovering an entire liquid hydrocarbon sample. In other words, each of the chemical components that make up the hydrocarbon sample are isolated and recovered. The present systems and methods utilize an accelerated solvent extractor. Conventionally, accelerated solvent extractors are used strictly as a solvent extraction tool. As is known, accelerated solvent extraction (ASE) is traditionally used for extraction of solid and semi-solid samples. ASE operates under high pressure in order to maintain the solvent in liquid phase during the extraction process and can be used in a wide range of different applications, including but not limited, pharmaceuticals, dietary supplements, food analysis, chemical applications, etc.

ASE can include the use of a sorb ent material, such as an adsorbent(s). As is known, an adsorbent is a solid substance used to collect solute molecules from a liquid or gas (e.g., hydrocarbon liquid sample of the present invention). Adsorption is often used to extract a species, such as chemical pollutants, by causing them to be attached to adsorbents, such as activated carbon or silica gel. In other words, an adsorbent is an insoluble material coated by liquid on the surface, including capillaries and pores.

In contrast to the conventional use of an ASE system, the systems and methods of the present application utilize the accelerated solvent extractor as a type of separation column for separating the various fractions of a hydrocarbon sample. In other words, the present systems and methods allow for the performance of a column chromatography (flash chromatography) method for separating the fractions of a liquid sample. The process is performed until the entire liquid sample has been separated into its fractions.

In the present systems and methods, a filter is inserted into an extraction cell of the accelerated solvent extractor. An adsorbent is activated via heating in a furnace of the accelerated solvent extractor, cooled, and then inserted into the extraction cell. A liquid sample, such as a liquid hydrocarbon sample, is then introduced into the extraction cell on top of the adsorbent, and the extraction cell is placed into a cell tray of the accelerated solvent extractor. A first fraction of the hydrocarbon sample (e.g., saturates fraction) is then extracted from the sample using a first solvent and is collected in a collection vial. One or more subsequent compounds (fractions) of the hydrocarbon sample (e.g., aromatic and resin fractions) are then extracted using one or more additional solvents such that the entire liquid hydrocarbon sample is extracted. While the term "extracted" is used herein, Applicant is using this term to generally convey that the present invention uses a selected solvent to separate compound classes that make up the sample by effectively isolating and removing a targeted compound class from the hydrocarbon sample. Prior to introduction of the liquid hydrocarbon sample into the extraction cell, asphaltenes (if present) can be removed from the liquid hydrocarbon sample via a deasphalting step.

Thus, methods of the present application effectively utilize the accelerated solvent extractor as a separation column for quickly separating the fractions of a liquid feeds. The present methods also limit the overall amount of solvents used to complete the fractionation due to the small sample size and the use of the accelerated solvent extractor. As such, due to the speed at which the present method can be completed and the limited amount of solvents used, the present methods limits a user's exposure to the potentially harmful solvents associated with the method.

The referenced systems and methods for separating and recovering an entire liquid hydrocarbon sample are now described more fully with reference to the accompanying drawings, in which one or more illustrated embodiments and/or arrangements of the systems and methods are shown. The systems and methods of the present application are not limited in any way to the illustrated embodiment and/or arrangement. It should be understood that the systems and methods as shown in the accompanying figures are merely exemplary of the systems and methods of the present application, which can be embodied in various forms as appreciated by one skilled in the art. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods.

Figure 1A:
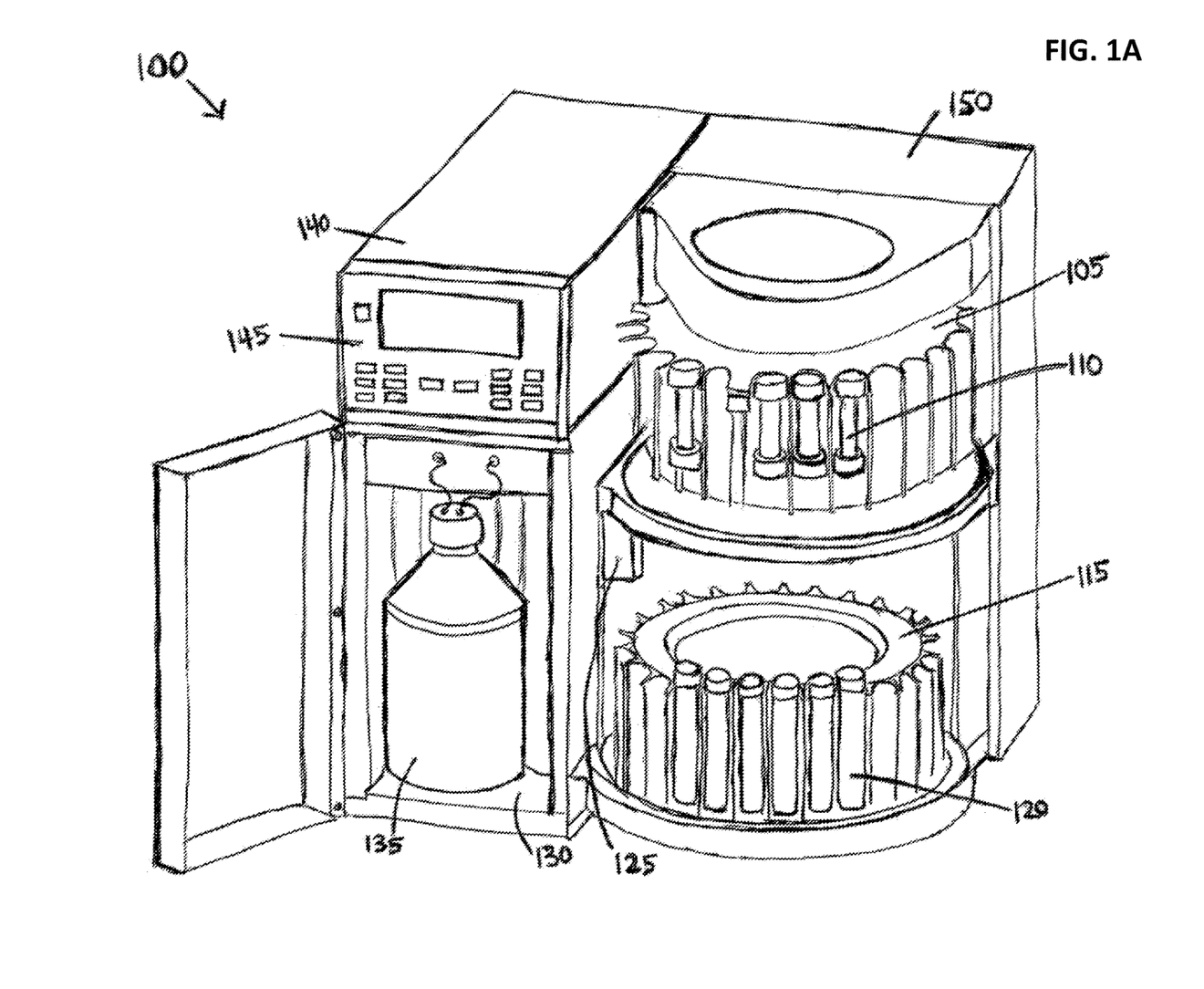
FIG. 1A displays an exemplary accelerated solvent extractor in accordance with one or more embodiments.

FIG. 1A displays an exemplary accelerated solvent extractor (ASE) 100 in accordance with one or more embodiments. Various models of ASEs can be used in accordance with one or more embodiments. For example, in at least one embodiment, the ASE can be the ASE® 200 Accelerated Solvent Extractor. The ASE can have numerous parts and settings (e.g., a solvent controller) as exemplified in the ASE® 200 Accelerated Solvent Extractor Operator's Manual and the ASE® Solvent Controller Installation Instructions, both of which are hereby incorporated by reference in their respective entireties as if set forth herein. Specifically, as shown in FIG. 1A, the ASE 100 can comprise a cell tray 105 and at least one extraction cell 110, the cell tray 105 being configured to securely hold a plurality of extraction cells 110. The ASE 100 further comprises a vial tray 115 and at least one collection vial 120, the vial tray 115 being configured to securely hold a plurality of collection vials 120. The vial tray 115 can also be configured to hold one or more rinsing vials. The cell tray 105 is positioned above the vial tray 115 such that the one or more extraction cells 110 are configured to selectively be in fluid communication with the one or more collection vials 120. Specifically, the cell tray 105 and the vial tray 115 are both configured to spin (rotate about a common axis) such that an extraction cell 110 can be in fluid communication with different collection vials 120 at different times. It will be readily understood that a master controller can be used to control rotation of the cell tray 105 and the vial tray 115 to the target locations. The one or more extraction cells 110 can be selectively in communication with the one or more collection vials 120 via the needle mechanism 125. Using the needle mechanism 125, the selected extraction cell 110 can transfer fluid to the selected collection vial 120. Specifically, the needle mechanism 125 pierces the septum of the selected collection vial 120 such that the fluid (extract) flows from the selected extraction cell 110 to the selected collection vial 120.

The ASE 100 can further include a solvent reservoir compartment 130 configured to hold a solvent bottle 135. In one or more implementations, one or more solvent bottles 135 can be held in a solvent controller (e.g., ASE® Solvent Controller) operatively connected to the ASE 100 such that multiple solvents can be used during the process. Specifically, the solvent controller can be configured to change the solvent bottle that is fluidly connected to the extraction cell 110 in between extractions. This allows different solvents to be used to extract (separate) in series different fractions of the liquid sample. The solvent controller can also be configured to perform other actions such as selecting the particular solvent to be used in a particular extraction or mixing two or more solvents together. The ASE 100 further comprises electronics 140 including a processor or microprocessor configured with code in the form of software, to execute a given instruction set, such as control of the trays 105, 115, the needle, pumps and other hardware, etc. The electronics 140 are operatively connected to the other components of the ASE such that when the processor or microprocessor executes a given instruction set, the processor can cause the other components of the ASE 100 to selectively perform their respective functions. The ASE 100 further comprises a display 145 that can comprise a screen and one or more actuators (e.g., buttons) such as a power switch. At the display 145, the user can turn the ASE 100 on and off and can enter settings/instructions via the actuators and/or the screen, where the settings/instructions cause the electronics 140 to configure the various components to perform their respective functions as discussed in further detail below. The ASE can include an oven (furnace) 150 for heating the extraction cell in accordance with one or embodiments. A temperature for the oven for a given separation method can be determined by the user via the display 145. The ASE 100 can also include one or more connections to an air source and/or a nitrogen gas source or supply (e.g., nitrogen gas tank).

Figure 1B:
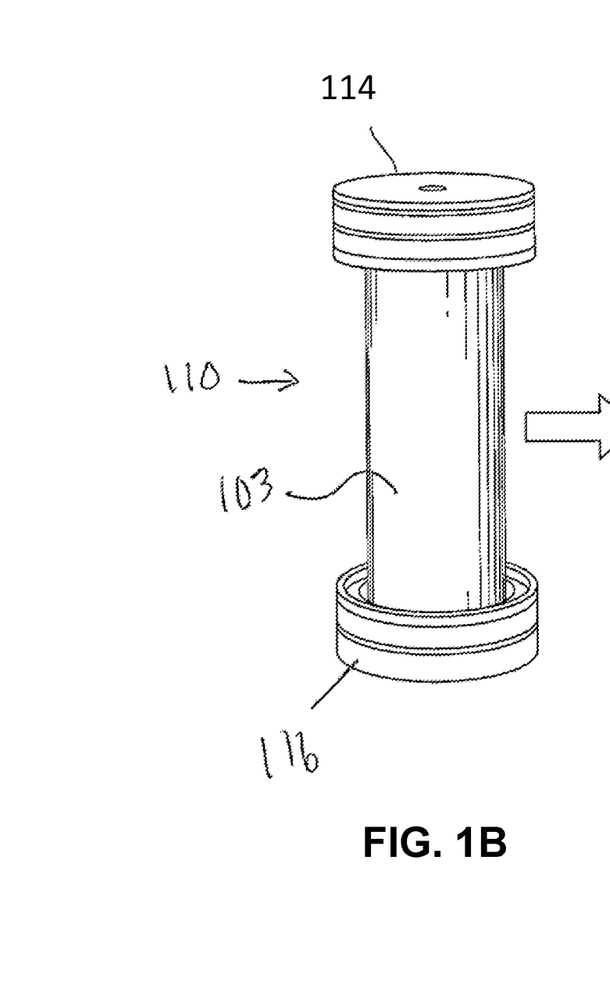
FIG. 1B is a perspective view of an exemplary extraction cell of the accelerated solvent extractor in accordance with one or more embodiments.
Figure 1C:
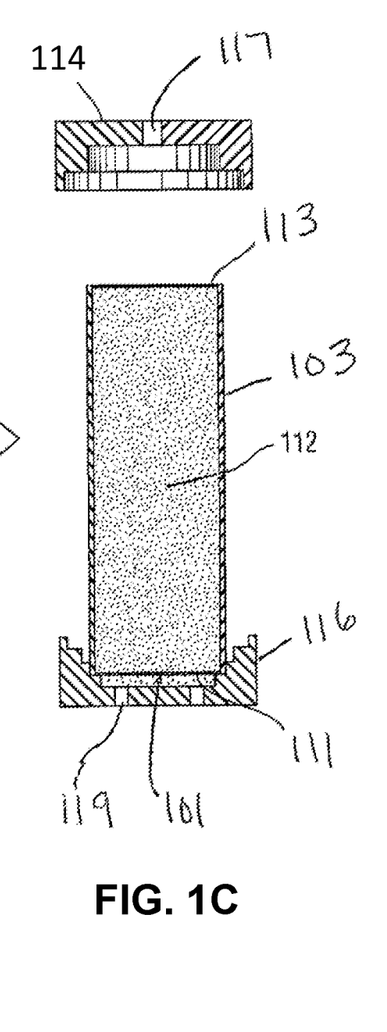
FIG. 1C is a cross-sectional view of the extraction cell of FIG. 1B.

FIGS. 1B and 1C display an exemplary extraction cell 110 of the accelerated solvent extractor in accordance with one or more embodiments. In one or more embodiments, to begin the method of the present application, a filter 111 is inserted into a bottom portion of the extraction cell 110. As is known, a conventional extraction cell 110 includes a tubular body 103 and a first end cap 114 and a second end cap 116 that closes off the tubular body. The tubular body can be a metal tube. The first end cap 114 is attached to the top of the tubular body using any number of conventional techniques, including but not limited to threads, etc., and similarly, the second end cap 116 is attached to the bottom of the tubular body. The first end cap 114 represents the inlet end and includes one or more openings 117 through which the fluid to be separated is introduced into the extraction cell 110. The second end cap 116 represents the outlet end and includes one or more openings 119 through which the separated fluid exits. A frit 101 is disposed within a recessed area of the second end cap 116. The frit 101 covers the opening(s) 119 but fluid can flow therethrough to allow discharge of the extracted fraction.

In one or more embodiments, the filter 111 can be a cellulose filter, although other types of filters can be used in accordance with at least one embodiment. A sorbent (adsorbent) material 112 used for packing the extraction cell 110 is then activated via heating in the oven (furnace) 150. In one or more embodiments, the adsorbent material comprises silica (e.g., 60 Å, 70-230 mesh). In one or more embodiments, the adsorbent is heated at a temperature of approximately 400° C. in an oven for approximately 4 hours during activation. As shown, the adsorbent 112 is packed into the tubular body 103 on top of the filter 111.

For instance, in at least one embodiment, the silica adsorbent is activated by heating in the furnace (oven) 150 for approximately 4 hours at approximately 400° C. Once the adsorbent 112 has been activated via heating, the adsorbent is allowed to cool. For example, in at least one embodiment in which the adsorbent is a silica adsorbent, the temperature of the furnace 150 is reduced to 150° C. to keep the silica adsorbent activated until it is needed for use in the ASE. The activation of the adsorbent material removes the moisture from the adsorbent material and keeps the material dry prior to insertion into the extraction cell. It should be noted that the heating time for the adsorbent, the heating temperature for the adsorbent in the furnace, and the temperature to which the adsorbent is "cooled" can vary depending on the type of adsorbent, as well as the type of liquid sample to be introduced into the extraction cell.

After cooling, at least a portion or the entire amount of the adsorbent 112 is inserted into the extraction cell 110 on top of the filter 111. In one or more embodiments, the portion of the adsorbent 112 can be wetted with a solvent prior to insertion into the extraction cell 110. For instance, in at least one embodiment, a cooled silica adsorbent 112 can be wetted with a hexane solvent prior to insertion into the extraction cell 110.

Once inserted into the extraction cell 110, the adsorbent occupies a substantial portion of the volume of the extraction cell 110. As used in this instance, "substantial" refers to a considerable, significant, and/or large portion of the volume of the extraction cell. For example, the adsorbent 112 can occupy greater than 75% of the volume of the extraction cell upon insertion. In at least one embodiment, when the adsorbent material 112 is inserted into the extraction cell 110, the adsorbent material 112 occupies 97 to 99% of the volume of the extraction cell 110. In at least one embodiment, the adsorbent material 112 occupies at least 95% by volume of the extraction cell 100 (i.e., 95% of the tubular body of the extraction cell 100). In at least one embodiment, the adsorbent material 112 occupies at least 98% by volume of the extraction cell 100. The remaining volume of the extraction cell 110 is filled by the liquid hydrocarbon sample 113 and the filter 111. Thus, unlike conventional ASE extraction cell preparation, the extraction cell 110 of the present invention consists substantially of the adsorbent material 112. This is in contrast to conventional ASE extraction cells in which the sample itself occupies a significant volume of the hollow interior of the extraction cell. In the present invention, the sample itself occupies a very small volume (space) within the tubular body. As a result and as described herein, the small sample size results in the sample being contained in a limited area, primarily along the top surface of the adsorbent material 112 and there can be some limited migration of the sample (depending upon the type of sample) into the very top layer of the adsorbent material 112.

Prior to introducing the liquid hydrocarbon sample 113 into the extraction cell, asphaltenes (if present in the hydrocarbon sample) are removed from the sample 113 via a deasphalting step. Asphaltenes are the portion of the hydrocarbon sample 113 that are not soluble in heptane. Asphaltenes are typically present in crude oil as well as in the heavy fractions of crude oil, such as vacuum gas oil, and vacuum residue fractions. In this way, the sample is preprocessed prior to introduction into the cell 110.

After insertion of the adsorbent material 112 into the extraction cell 110, the liquid hydrocarbon sample 113 to be separated is introduced into the extraction cell 110. The hydrocarbon sample 113 is introduced at the top of the adsorbent material 112 in the extraction cell. Upon introduction into the extraction cell 110, the sample 113 quickly spreads onto the first few millimeters (e.g., initial 5 millimeters) of the adsorbent material 112 on the top portion of the cell 110 and remains there. In one or more embodiments, the hydrocarbon sample 113 is contained within a top 10% by volume of the adsorbent material 112. In one or more embodiments, the liquid hydrocarbon sample 113 can be a diesel fuel sample, a crude oil sample, or a vacuum gas oil (VGO) sample. More viscous samples, such as crude oil tend to penetrate the adsorbent material 112 less than more liquid samples, such as diesel fuel. In any event, as a result of the small sample size, the sample can remain in the upper reaches of the adsorbent material 112 (e.g., upper 10% area of the adsorbent material 112) before the extraction process is initiated.

In one or more embodiments, a relatively small amount of hydrocarbon sample is introduced into the extraction cell 110. Unlike traditional ASE processing, the sample to be extracted in the present invention occupies only a very small fraction of the extraction cell in that the sample is typically less than 1 gram (e.g., 0.1 gram), while the adsorbent material that occupies most of the cell has a volume and weight that is vastly greater. For example, a 0.1-gram sample of diesel fuel or crude oil can be introduced into the extraction cell at the top of the adsorbent material. In one or more embodiments, the mass of the adsorbent material is in the range of approximately 3 grams to approximately 20 grams. In at least one embodiment, the mass of the adsorbent material can be approximately 15.5 grams (e.g., 15.5 grams of silica). In one or more embodiments, the hydrocarbon sample 113 can occupy less than 3% of the volume of the extraction cell 110. In certain embodiments, the hydrocarbon sample 113 can occupy less than 2% of the volume of the extraction cell 110. In at least one embodiment, the hydrocarbon sample 113 can occupy less than 1% of the volume of the extraction cell 110. The hydrocarbon sample 113 can be introduced into the extraction cell 110 using a pipette (e.g., glass pipette) and the sample 113 is initially delivered to the top exposed surface of the adsorbent material 112. In one or more embodiments, the adsorbent can occupy 97% to 99% of the volume of the extraction cell (e.g., volume of the tubular body of the extraction cell) In at least one embodiment, the adsorbent material can occupy at least 90% by volume of the tubular body of the extraction cell 100.

After introducing the sample 113 into the extraction cell 110, the filled extraction cell 110 is closed (end cap 114 is attached to the tubular body) and placed in cell tray 105 of the ASE 100. In placement of the extraction cell in the cell tray 105, the extraction cell 110 is kept in the sample position as during introduction of the hydrocarbon sample— an upward position in which the sample 113 is on top of the adsorbent material 112.

With reference again to FIG. 1A, once the extraction cell loaded with the hydrocarbon sample is loaded into the cell tray 105, the separation of the hydrocarbon sample into fractions begins by operation of the ASE 100. In one or more embodiments, empty syringe rinsing vials are placed in the vial tray 115 and are used to collect waste solvent, such as the solvent used for flushing. Additionally, in one or more embodiments, the one or more solvent bottles 135 to be used in the separation process each have at least 200 mL of their respective solvents.

The respective fractions of the liquid hydrocarbon sample 113 are extracted sequentially. For example, in one or more embodiments, the saturate fraction (a first fraction) of the hydrocarbon sample 113 is extracted first using a first solvent. In other words, the first solvent is introduced into the extraction cell 110 and the solvent interacts with the liquid hydrocarbon sample (e.g., the first fraction dissolves into the first solvent) such that the fraction to be extracted passes through the filter and into the collection vial 120 via the needle mechanism 125. In other words, the sample 113 is pushed through the adsorbent material 112 (packing material) by the solvent. As the solvent is introduced into the top of the cell, it interacts with the sample 112 and dissolves the targeted fraction of the sample and then the continued introduction of solvent causes the dissolved fraction and solvent to be washed through the adsorbent material 112 and ultimately the filter 111. Because of the difference of affinity of the compounds towards the adsorbent (packing) material 112 and the different solvents used to extract the different fraction as described herein, every solvent will manage to push a different class of compounds out of the cell until all classes of compounds have been removed from the cell.

The entire process relies on completion in terms of interactions between the sample, the adsorbent material, and the solvent used. For example, in a first extraction step when the first solvent (e.g., hexane) is used for extraction of the saturates fraction, the saturates fraction will preferentially move from the adsorbent material to the first solvent phase (e.g., hexane phase) while the aromatics and resins fractions remain with the adsorbent material. After the hexane loaned with the saturates has been collected in the first vial, the second solvent is introduced into the extraction cell. The aromatics will then transfer from the adsorbent material to the second solvent because their affinity toward the second solvent is greater than their affinity toward the adsorbent material. The resins fraction is removed similarly using a third solvent.

Each solvent is selected so that it targets the fraction that is intended to be extracted, while leaving behind the other fractions that are to be subsequently fractionated. In one or more embodiments, the solvent for extracting the saturate fraction can be hexane; however, other suitable solvents can be equally used. In at least one embodiment, the hexane is high-performance liquid chromatography (HPLC) grade hexane. In one or more embodiments, other solvents can be used for the extraction of the saturate fraction, including but not limited to cyclohexane, heptane, isooctane, or other light alkanes.

In at least one embodiment, the aromatics fraction of the hydrocarbon sample 113 is the second fraction to be extracted. The aromatics fraction is extracted using a second solvent, which is generally different from the solvent (first solvent) used to extract the saturates fraction. Specifically, following extraction of the first fraction, the second solvent is introduced into the extraction cell 110 as from one solvent bottle 135. The second solvent then interacts with the remaining portions of the liquid sample (i.e., the original liquid sample minus the saturate fraction) such that the aromatics fraction passes through the filter. Before introduction of the second solvent into the extraction cell 110, the cell tray 105 (or the vial tray) can be shifted (e.g., spun) such that the extraction cell is placed in fluid connection with a different collection vial 120 via the needle mechanism 125. As such, when the aromatics fraction passes through the filter in the extraction cell 110, it can be introduced into a different collection vial 120 than the one in which the saturates fraction was introduced. In one or more embodiments, the second solvent is toluene. In at least one embodiment, the toluene is American Chemical Society (ACS) grade toluene. In one or more embodiments, other solvents can be used as the second solvent, such as a blend of toluene and cyclohexane (e.g., 95 toluene/5 cyclohexane). In at least one embodiment, one or more sulfur compounds in the hydrocarbon sample 113 are extracted with the aromatics fractions using the second solvent. In certain embodiments, sulfur compounds can be extracted with both the aromatic and resins fractions. The chemical makeup of the sulfur compounds extracted with the aromatic and resins fractions, is based on their respective solubilities in a given solvent.

In at least one embodiment, one or more other fractions can be extracted from the hydrocarbon sample. For instance, in certain hydrocarbon samples, a resin fraction is the third fraction to be extracted, and it can be extracted using a specified solvent and specified operational parameters of the ASE. Solvents that can be used for the extraction of the resin fraction from the hydrocarbon sample include, but are not limited to acetone, chloroform, methanol, and a blend of toluene and methanol (e.g., 1:4 toluene to methanol). Further, in at least one embodiment, one or more nitrogen compounds in the hydrocarbon sample are extracted with the resin fraction due to the similar solubility of the nitrogen compounds and the resin fraction in the solvent used for resin extraction. In embodiments in which saturate, aromatic, and/or resin fractions are extracted from the hydrocarbon sample, the respective fractions are extracted sequentially in separate stages using respective operational parameters for the ASE. In one or more embodiments of the present method, the entire liquid hydrocarbon sample is extracted such that essentially no part of the hydrocarbon sample remains in the cell after the various fractions are removed.

As the various fractions of the hydrocarbon sample are sequentially extracted based on the different solvents used, operational parameters for the ASE can vary between the sequential extractions. In one or more embodiments, a flushing step is also performed between the extractions of the various fractions. In this step, nitrogen gas is used to flush the needle and/or the extraction cell of the previous solvent from the previous extraction step prior to introduction of the next solvent.

Figure 2:
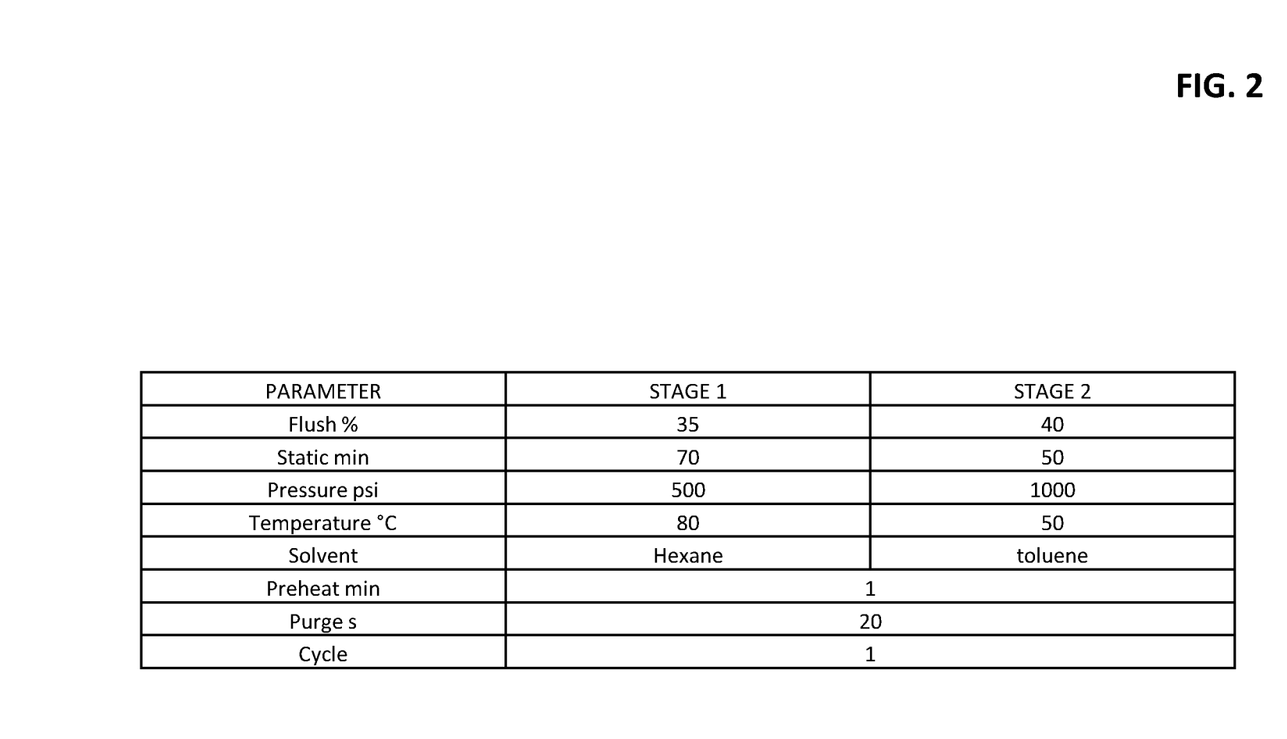
FIG. 2 displays a table of exemplary method parameters for separation of saturate and aromatic fractions from a hydrocarbon sample using the accelerated solvent extractor in accordance with one or more embodiments.

The separating and recovering process of the present application is performed until the original liquid sample has been completely fractionated and no fractions remain in the extraction cell 110. For instance, other operational parameters that can be varied between the respective extractions include the amount of solvent flushed through the cell (flush percentage), the static solvent extraction period, the amount of fluid pressure in the cell during extraction, the temperature at which the cell is heated, the preheating period, the amount of time nitrogen gas purges the cell (purge time), and the number of cycles for the respective extraction. FIG. 2 shows a table of the exemplary parameters for the ASE in embodiments of the present method in which the saturates fraction and the aromatics fraction are extracted sequentially. In FIG. 2, stage 1 represents exemplary parameters for the ASE for extracting the saturates fraction from the exemplary hydrocarbon sample, while stage 2 represents exemplary parameters for extracting the aromatics fraction. In the example of FIG. 2, the flush percentage, static solvent extraction period, amount of fluid pressure in the cell, the temperature of the cell, and the type of solvent vary between stage 1 (extraction of saturates) and stage 2 (extraction of aromatics). In contrast, the preheating period, the purge time, and the number of cycles remains the same for both stages. It should be understood that, depending on the type of hydrocarbon sample and the type of the fractions to extracted, each of the above operational parameters can be varied or the same between the respective extraction stages.

As a result of the chemical makeup of the sample, the entire sample can be separated into separate compound classes and upon completion of the fractionization process, the original sample has been removed from the cell which is in contrast to the conventional ASE process in which at least a portion of the sample remains in the cell.

According to at least one exemplary embodiment, a method of separating and recovering a liquid hydrocarbon sample using an accelerated solvent extractor can be performed in the following manner. An extraction cell that includes a tubular body packed with a filter at a bottom end and an adsorbent material disposed on top of the filter is prepared, such that the adsorbent material occupies at least 90% by volume of the tubular body. The hydrocarbon sample is then introduced on top of the adsorbent material in the extraction cell. The extraction cell comprising the hydrocarbon sample is placed into a cell tray of the accelerated solvent extractor. At least one extraction is then performed using at least one solvent resulting in one or more fractions being individually extracted and collected. In certain implementations, the adsorbent material occupies at least 95% by volume of the tubular body. In at least one implementation, the adsorbent material occupies at least 98% by volume of the tubular body. In one or more implementations, the step of introducing the hydrocarbon sample results in the hydrocarbon sample being contained within a top 10% by volume of the adsorbent material.

Referring again to FIG. 1A, each of the respective fractions that are extracted from the hydrocarbon sample can be collected in separate collection vials 120 such that they can be further analyzed. When the sequential extractions are complete, the collection vials 120 containing the respective fractions are each placed under nitrogen gas (via the nitrogen gas source) in a fume hood to remove the respective solvents. In one or more embodiments, the nitrogen gas source of the ASE 100 can comprise nitrogen gas having a high purity percentage, such as 99.9% or higher (e.g., 99.95%). After the respective solvents are removed from the collection vials via the nitrogen gas, the respective fractions can be further analyzed. For instance, in one or more embodiments, the respective fractions can be qualitatively analyzed via an analytical technique (e.g., chromatography) to determine the compositions of the respective fractions. In one or more embodiments, the analytical technique can be selected from mass spectrometry, NMR spectroscopy, gas chromatography, liquid chromatography, and supercritical chromatography.

Figure 3A:
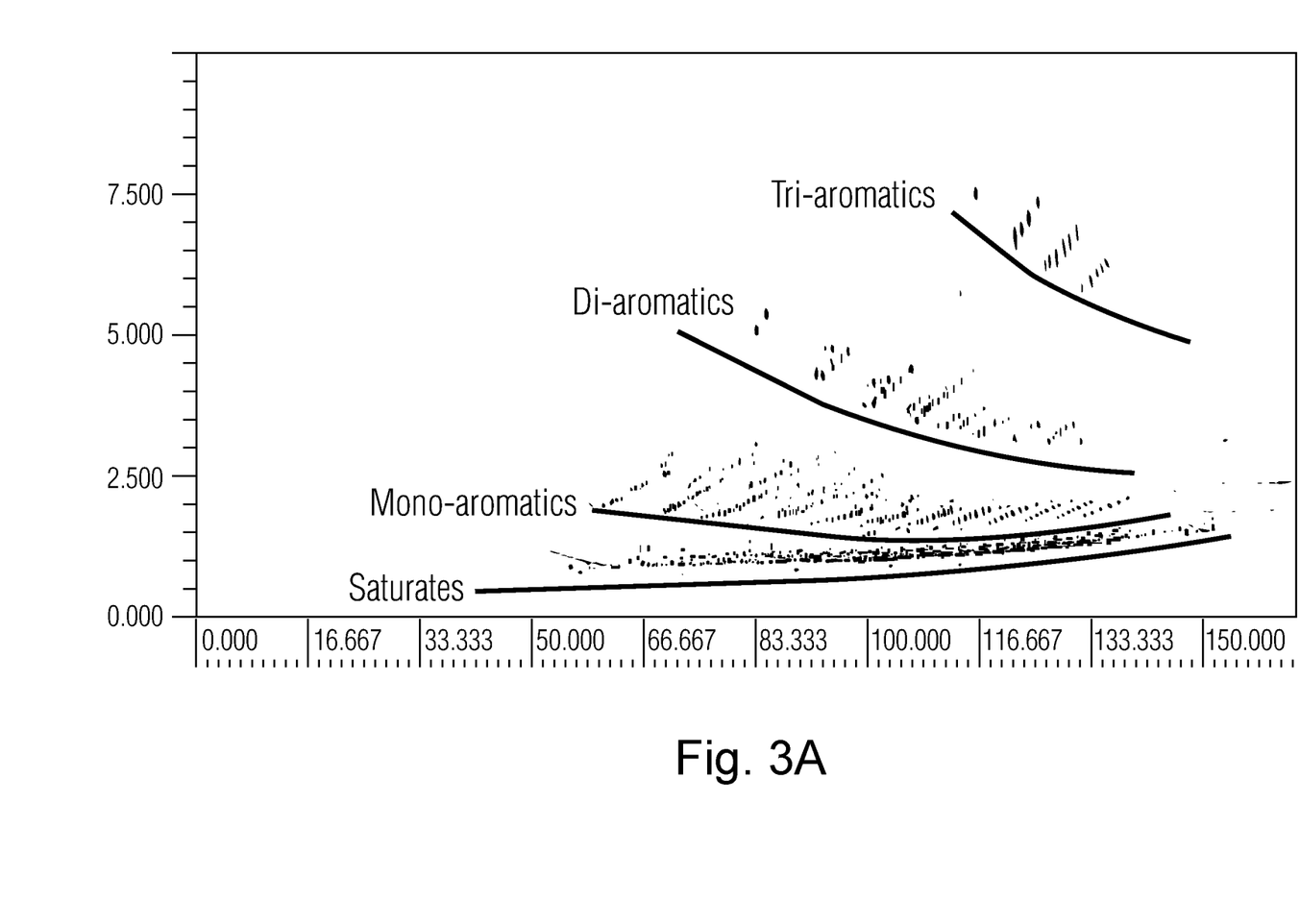
FIG. 3A displays a chromatogram of an exemplary diesel fuel sample in accordance with one or more embodiments.
Figure 3B:
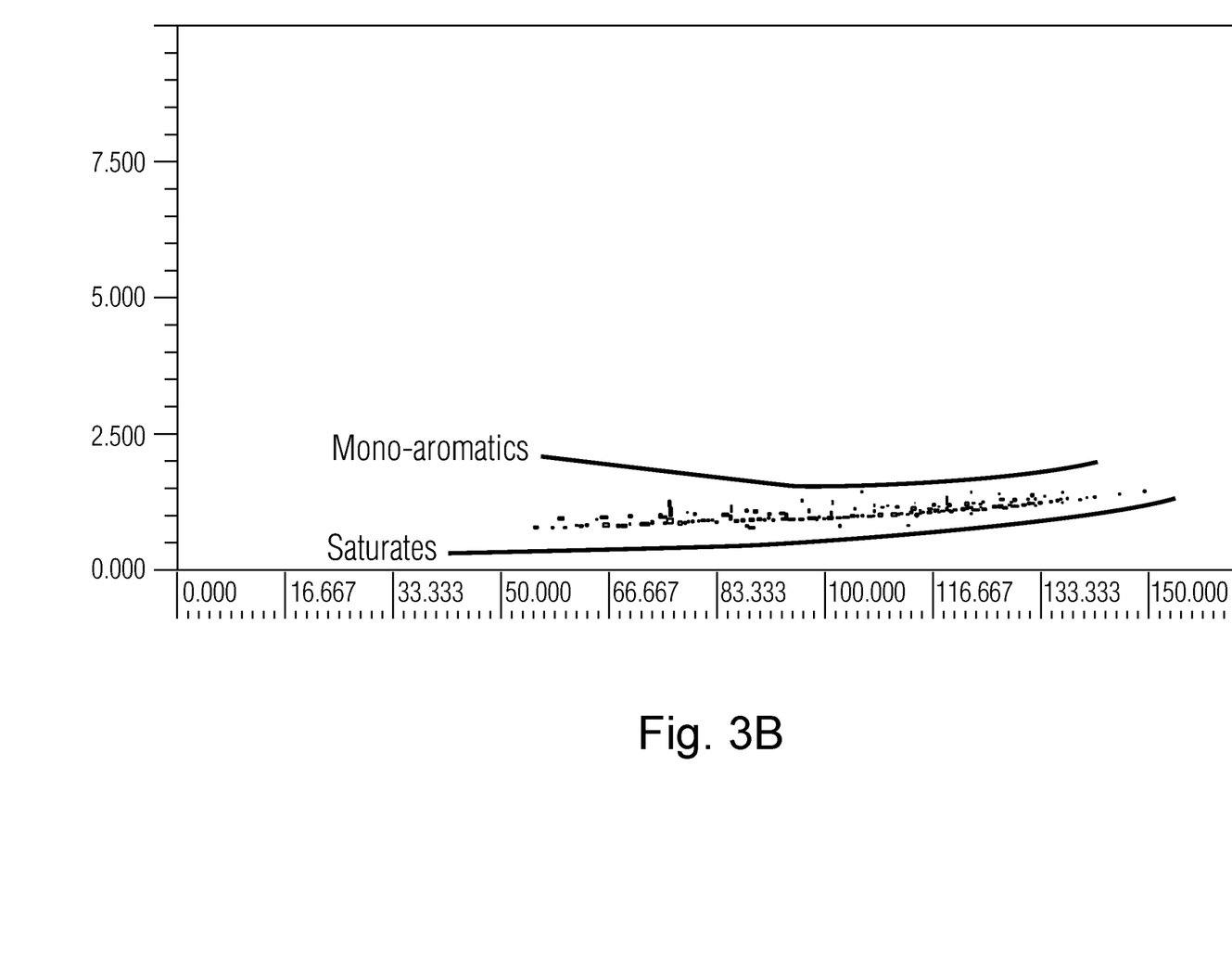
FIG. 3B displays a chromatogram of a separated saturates fraction of the exemplary diesel fuel sample in accordance with one or more embodiments.
Figure 3C:
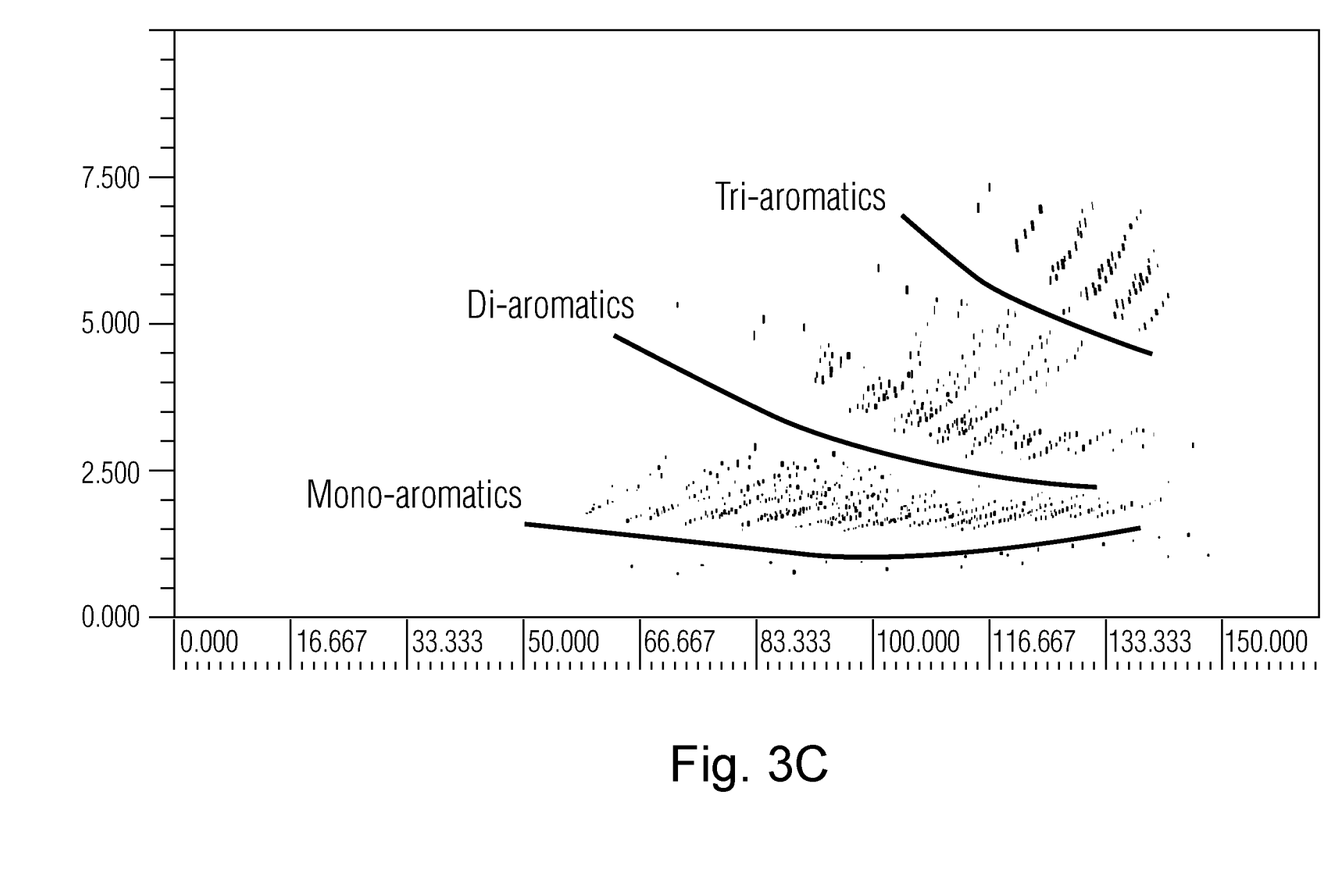
FIG. 3C displays a chromatogram of a separated aromatics fraction of the exemplary diesel fuel sample in accordance with one or more embodiments.

The effectiveness of the present method for separating diesel samples is shown in the example of FIGS. 3A-3C. FIGS. 3A-3C display exemplary chromatograms for an exemplary diesel fuel sample that underwent the disclosed separation method in accordance with one or more embodiments. Specifically, FIG. 3A displays a chromatogram of the full diesel fuel sample as a reference, and FIGS. 3B and 3C display chromatograms of the separated saturates and aromatics fractions, respectively, after the diesel fuel sample underwent the present separation method. To produce chromatograms of FIGS. 3A-3C, the full diesel fuel sample and the resulting saturate and aromatic fractions underwent comprehensive two-dimensional gas chromatography equipped with a flame ionization detector for diesel fractions. As shown in FIGS. 3B and 3C, the separation of the saturates and aromatics fractions using the present method were successful, as there were only trace amounts of overlap between the two fractions (i.e., trace amounts of mono-aromatics shown in the saturates chromatogram of FIG. 3B), which is an indication of a high-quality separation.

Figure 4:
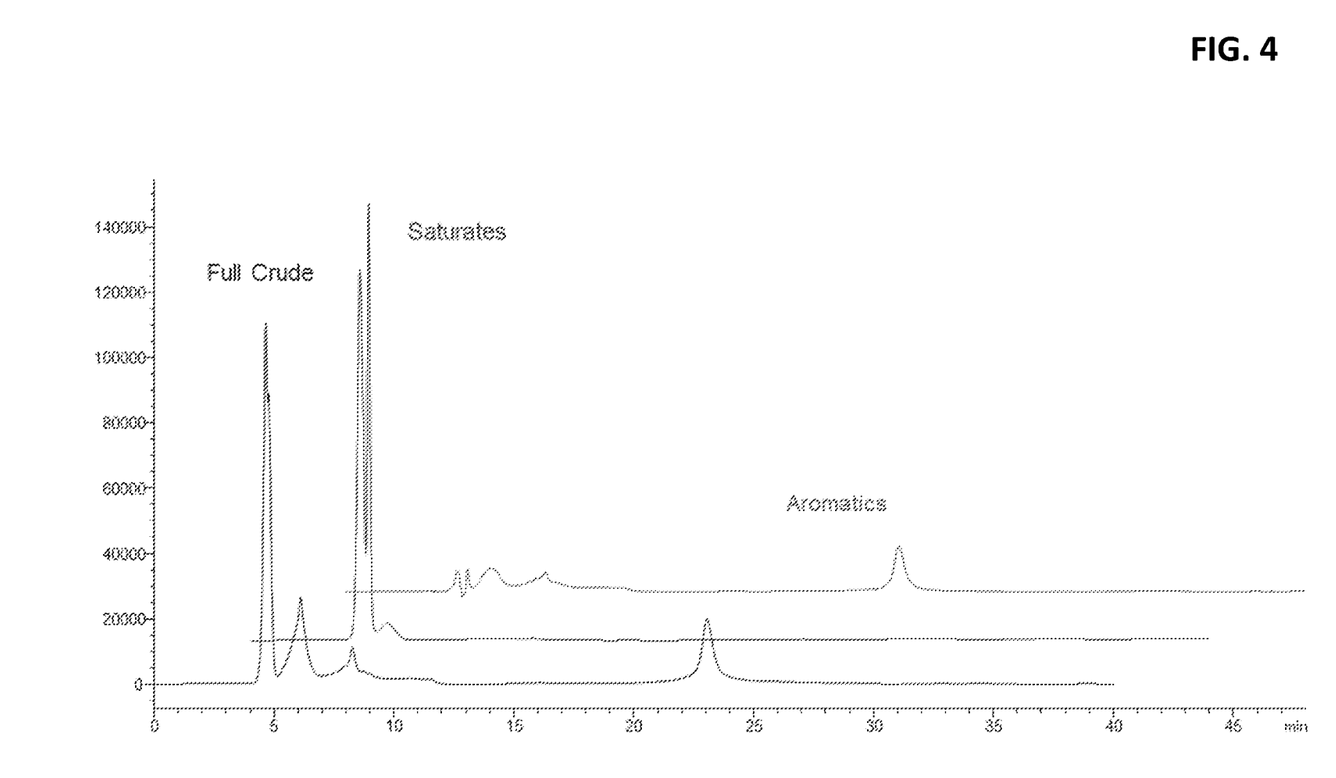
FIG. 4 displays chromatograms of an exemplary crude oil sample, the chromatograms resulting from an analysis via high-performance liquid chromatography with a refractive index detector (HPLC-RI) in accordance with one or more embodiments.

The effectiveness of the present method for separating crude oil fractions is shown in the example of FIG. 4. FIG. 4 displays exemplary chromatograms for an exemplary crude oil sample (de-asphalted crude oil) that underwent the disclosed separation method in accordance with one or more embodiments. In this example, separated saturates and aromatics fractions from the crude oil sample were analyzed using high-performance liquid chromatography equipped with a refractive index detector (HPLC-RI). FIG. 4 compares the chromatograms of the full crude oil sample with the chromatograms of the resulting saturates and aromatics fractions. As shown in FIG. 4, only trace amounts of mono-aromatics are found in the saturate chromatogram, while the aromatics chromatogram shows an absence of a saturate peak. Accordingly, the chromatograms of FIG. 4 indicate that there were only trace amounts of overlap between the two fractions, indicating that the separation of the two fractions was effective.

In the above examples, overlap between the saturate and aromatic fractions were maintained at a value of less than 15% or less, indicating that the present separation method is effective.

As shown in these examples, the present disclosure provides a novel method for separating liquid hydrocarbon samples into fractions. In the present method, the ASE acts not as a solvent extractor, but rather as a type of separation column. Moreover, in the present method, the entire liquid hydrocarbon sample can be separated or extracted such that essentially no part of the hydrocarbon sample remains in the extraction cell of the ASE. This is accomplished, in part, by using sequential solvents such that each solvent pushes a different class of compound in the sample out of the extraction cell and into separate collection vials due to the varying affinities of the different classes of compounds to the various solvents. The present method is in contrast with conventional uses of the ASE (e.g., solvent extraction methods) in which the extraction cell is filled with the sample to be extracted as well as a dispersing agent (e.g., sand, diatomaceous earth). As such, in conventional uses of the ASE, the entire contents of the extraction cell cannot be extracted as at least a portion the sample blended with the dispersing agent remains in the cell and cannot be extracted.

The present method provides is faster and more efficient method than conventional separation and quantification methods, such as gravimetric quantification methods that use column chromatography. The present method also limits a user's exposure to harmful chemicals relative to gravimetric quantification methods, which require an all-day experiment with longer exposure time to chemicals. Further, the present methods use significantly lower amounts of solvents and adsorbent materials relative to conventional methods.

Results gathered from the present method (e.g., compositional analysis of the hydrocarbon sample and the separated fractions) can also be beneficially used for upstream operations, such as modelling and assessing petroleum reservoirs in terms of producibility and oil valuation. Further, in addition to providing physical and refining information, the compositional analysis of the liquid hydrocarbon sample can also support flow rate calculations and characterization of compartmentalization for oil reservoirs. The ability of the present method to accurately separate the fractions of a hydrocarbon sample also allows for further downstream analysis of the separated fractions at a molecular level.

Although much of the foregoing description has been directed to systems and methods for separating and recovering a liquid hydrocarbon sample, the system and methods disclosed herein can be similarly deployed and/or implemented in scenarios, situations, and settings far beyond the referenced scenarios. For example, other types of liquid samples besides hydrocarbon samples can also be utilized in the present systems and methods. It should be further understood that any such implementation and/or deployment is within the scope of the system and methods described herein.

It is to be further understood that like numerals in the drawings represent like elements through the several figures, and that not all components and/or steps described and illustrated with reference to the figures are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms ""including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed:

1. A method of separating and recovering an entire liquid hydrocarbon sample using an accelerated solvent extractor, the method comprising:
    inserting a filter into a bottom portion of an extraction cell of the accelerated solvent extractor;
    inserting at least an adsorbent into the extraction cell, wherein the adsorbent occupies a substantial portion of the volume of the extraction cell;
    introducing the hydrocarbon sample on top of the adsorbent in the extraction cell;
    placing the extraction cell comprising the hydrocarbon sample into a cell tray of the accelerated solvent extractor;
    extracting a saturate fraction of the hydrocarbon sample using a first solvent, wherein the saturate fraction is collected in a first collection vial;
    extracting an aromatics fraction of the hydrocarbon sample using a second solvent, wherein the aromatics fraction is collected in a second collection vial; and
    extracting a resins fraction of the hydrocarbon sample using a third solvent, wherein the resins fraction is collected in a third collection vial,
    wherein the entire liquid hydrocarbon sample is extracted.

2. The method of claim 1, further comprising:
    activating the adsorbent via heating within an oven of the accelerated solvent extractor and cooling the activated adsorbent prior to insertion of the adsorbent into the extraction cell.

3. The method of claim 2, further comprising:
    wetting the cooled, activated adsorbent with a solvent prior to insertion into the extraction cell.

4. The method of claim 3, wherein the adsorbent material comprises silica.

5. The method of claim 4, wherein the solvent for wetting the cooled, activated silica adsorbent is hexane.

6. The method of claim 4, wherein the silica adsorbent is heated at a temperature of approximately 400° C. in the oven for approximately 4 hours during activation.

7. The method of claim 6, wherein the oven is subsequently cooled to 150° C. to cool the silica adsorbent.

8. The method of claim 1, further comprising:
    placing the first, second, and third collection vials under nitrogen gas to remove the first, second, and third solvents from the collected saturate, aromatic, and resins fractions, respectively.

9. The method of claim 8, wherein the saturate, aromatic, and resin fractions are extracted sequentially from the liquid hydrocarbon sample.

10. The method of claim 1, further comprising:
    qualitatively analyzing the extracted fractions to determine the compositions of the respective fractions, wherein the extracted fractions are analyzed via an analytical technique selected from the group consisting of mass spectrometry, NMR spectroscopy, gas chromatography, liquid chromatography, and supercritical chromatography.

11. The method of claim 1, wherein the first solvent comprises hexane and the second solvent comprises toluene.

12. The method of claim 1, wherein the extraction of the saturate fraction is performed at a different temperature and pressure than the extraction of the aromatic fraction and the resins fraction.

13. The method of claim 1, wherein the liquid hydrocarbon sample is a diesel fuel sample.

14. The method of claim 1, wherein the liquid hydrocarbon sample is a crude oil sample.

15. The method of claim 1, wherein the step of extracting the saturate fraction comprises introducing the first solvent into the extraction cell, whereby the first solvent interacts with the liquid hydrocarbon sample and causes the saturate fraction to pass through the filter and into the first collection vial;
    wherein the step of extracting the aromatic fraction comprises introducing the second solvent into the extraction cell, whereby the second solvent interacts with the liquid hydrocarbon sample and causes the aromatic fraction to pass through the filter and into the second collection vial; and
    wherein the step of extracting the resins fraction comprises introducing the third solvent into the extraction cell, whereby the third solvent interacts with the liquid hydrocarbon sample and causes the resins fraction to pass through the filter and into the third collection vial.

16. The method of claim 15, wherein the extractions of the respective fractions are performed at different respective temperatures and pressures.

17. The method of claim 1, wherein the first solvent is selected from the group consisting of: hexane, cyclohexane, heptane, and isooctane.

18. The method of claim 1, wherein the second solvent is toluene or 95:5 blend of toluene and cyclohexane.

19. The method of claim 1, wherein the third solvent is selected from the group consisting of: acetone, chloroform, methanol, and a 1:4 blend of toluene and methanol.

20. The method of claim 1, further comprising:
    flushing the extraction cell with nitrogen gas between the extractions of each of the saturate fraction, the aromatics fraction, and the resins fraction, wherein the nitrogen gas flushes the extraction cell of the solvent present from the previous extraction step.

21. The method of claim 1, wherein the adsorbent occupies 97 to 99% of the volume of the extraction cell and wherein the hydrocarbon sample occupies less than 3% of the volume of the extraction cell.

22. A method of separating and recovering a liquid hydrocarbon sample using an accelerated solvent extractor, the method comprising:
    preparing an extraction cell that includes a tubular body that is packed with a filter at a bottom end and an adsorbent material that is disposed on top of the filter, wherein the adsorbent material occupies at least 90% by volume of the tubular body;
    introducing the hydrocarbon sample on top of the adsorbent material in the extraction cell;
    placing the extraction cell comprising the hydrocarbon sample into a cell tray of the accelerated solvent extractor; and
    performing extractions of a saturate fraction, an aromatics fraction, and a resins fraction using at least one solvent resulting in the fractions being individually extracted and collected.

23. The method of claim 22, wherein the adsorbent material occupies at least 95% by volume of the tubular body.

24. The method of claim 22, wherein the adsorbent material occupies at least 98% by volume of the tubular body.

25. The method of claim 22, wherein the step of introducing the hydrocarbon sample results in the hydrocarbon sample being contained within a top 10% by volume of the adsorbent material.

26. The method of claim 22, wherein the step of performing extractions comprises extracting the saturate fraction using a first solvent, extracting the aromatics fraction using a second solvent, and extracting the resins fraction using a third solvent.

\* \* \* \* \*